(12) United States Patent
Alexander et al.

(10) Patent No.: US 8,897,890 B2
(45) Date of Patent: Nov. 25, 2014

(54) IMPLANTABLE MEDICAL ELECTRICAL LEAD AND CONNECTOR ASSEMBLY

(71) Applicant: Medtronic, Inc., Minneapolis, MN (US)

(72) Inventors: James A. Alexander, Shorewood, MN (US); James M. Olsen, Plymouth, MN (US); Chad Q. Cai, Woodbury, MN (US); Richard T. Stone, Minneapolis, MN (US); James G. Skakoon, St. Paul, MN (US); Kristin J. Malekkhosravi, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/872,328

(22) Filed: Apr. 29, 2013

(65) Prior Publication Data
US 2013/0245735 A1    Sep. 19, 2013

Related U.S. Application Data

(62) Division of application No. 11/737,927, filed on Apr. 20, 2007, now Pat. No. 8,433,422.

(51) Int. Cl.
*A61N 1/00* (2006.01)
*A61N 1/375* (2006.01)
*A61N 1/05* (2006.01)
*A61N 1/08* (2006.01)

(52) U.S. Cl.
CPC ............ *A61N 1/05* (2013.01); *A61N 1/3752* (2013.01); *A61N 2001/083* (2013.01); *A61N 2001/086* (2013.01)
USPC ............... 607/116; 607/115; 607/36; 607/37; 607/38

(58) Field of Classification Search
CPC ...... A61N 1/05; A61N 1/0565; A61N 1/3968
USPC ..................... 607/115, 116, 36–38
See application file for complete search history.

(56) References Cited

U.S. PATENT DOCUMENTS 4,971,057 A * 11/1990 Theres ............................. 607/37
7,076,302 B2 * 7/2006 Scheiner ......................... 607/27
2004/0267328 A1 * 12/2004 Duffin et al. .................... 607/37

* cited by examiner

*Primary Examiner* — Michael Kahelin
*Assistant Examiner* — Mallika D Fairchild

(57) ABSTRACT

An implantable system that includes a lead and an implantable signal generator wherein the plurality of electrical contacts and the plurality of insulating regions on the lead, and the plurality of electrical connectors and the plurality of electrical insulators in the connector block are configured so that each of the plurality of electrical contacts form operable connections to the electronic circuitry through each of the plurality of electrical connector, and the insulating regions and the electrical insulators electrically isolate adjacent operable connections. Leads, and methods are also disclosed.

10 Claims, 6 Drawing Sheets

IMPLANTABLE MEDICAL ELECTRICAL LEAD AND CONNECTOR ASSEMBLY

FIELD

Implantable medical electrical lead and connector assembly, more specifically, an implantable medical electrical lead and connector assembly having variable spacing of the electrical contacts.

BACKGROUND

The medical device industry produces a wide variety of electronic and mechanical devices for treating medical conditions. Commonly used neuromodulators include an implantable signal generator and at least one lead. Such devices are commonly utilized to treat numerous conditions in various portions of the body.

Magnetic resonance imaging (MRI) is commonly used to diagnose many disorders and conditions in many parts of the body. MRI scans utilize strong magnetic fields to produce diagnostic images. Concerns have arisen regarding possible undesirable interactions between the environment created during an MRI scan and implantable medical devices. Implantable medical devices and components thereof are being fabricated to alleviate any possible issues in an MRI environment. However, without a lockout, non-MRI safe components can be compatible with MRI safe components.

Therefore, there remains a need for MRI safe implantable medical devices and components thereof that can only be used with other MRI safe components.

BRIEF SUMMARY

An implantable system comprising: a lead, wherein the lead comprises: a) a lead body having a proximal end, a proximal portion, a distal portion, and a major axis; b) a plurality of electrodes located at the distal portion of the lead body; c) a plurality of electrical contacts located at the proximal portion of the lead body, wherein each of the plurality of electrical contacts has a contact length along the major axis of the lead body; d) a plurality of insulating regions located at the proximal portion of the lead body, wherein each of the plurality of insulating regions has an insulating length along the major axis of the lead body; and e) a plurality of conductive elements that operably couple the plurality of electrodes to the plurality of electrical contacts, wherein the plurality of the electrical contacts and the plurality of the insulating regions are configured so that the plurality of insulating regions electrically isolate the electrical contacts, and wherein either one of the plurality of insulating lengths is different from the other insulating lengths or one of the plurality of contact lengths is different from the other contact lengths; and an implantable signal generator, wherein the implantable signal generator comprises: a) electronic circuitry; and b) a connector block comprising: i. a lumen having a major axis, wherein the lumen is configured to receive at least a portion of the lead; ii. a plurality of electrical connectors each having an electrical connector length along the major axis of the lumen, wherein the plurality of electrical connectors are operably coupled to the electronic circuitry, iii. a plurality of electrical insulators each having an electrical insulator length along the major axis of the lumen, wherein either one of the plurality of electrical connector lengths is different from the other electrical connector lengths or one of the plurality of electrical insulator lengths is different from the other electrical insulator lengths, wherein the plurality of electrical contacts and the plurality of insulating regions on the lead, and the plurality of electrical connectors and the plurality of electrical insulators in the connector block are configured so that the plurality of electrical contacts form operable connections to the electronic circuitry through the plurality of electrical connector, and the insulating regions and the electrical insulators electrically isolate adjacent operable connections.

A process of determining whether a lead that has been operably coupled to an implantable signal generator is an MRI safe lead, wherein the lead comprises: a) a lead body having a proximal end, a proximal portion and a distal portion; b) a plurality of electrodes located at the distal portion of the lead body; c) a plurality of electrical contacts located at the proximal portion of the lead body, wherein each of the plurality of electrical contacts has a contact length along the lead body; d) a plurality of insulating regions located at the proximal portion of the lead body, wherein each of the plurality of insulating regions has an insulating length along the lead body; and e) a plurality of conductive means that electrically couple the plurality of electrodes to the plurality of electrical contacts, wherein either one of the plurality of insulating lengths is different from the other insulating lengths or one of the plurality of contact lengths is different from the other contacts lengths, wherein the implantable signal generator comprises: a) electronic circuitry; b) a connector block configured to receive the MRI safe lead; c) a plurality of electrical connectors within the connector block, wherein the plurality of electrical connectors are operably coupled to the electronic circuitry, the method comprising the steps of: i. inserting a lead into the connector block of the implantable signal generator; ii. measuring at least one characteristic of one of the plurality of electrical contacts; iii. determining whether the at least one measured characteristic of the one of the plurality of electrical contacts is within a range that corresponds to the electrical contact being properly electrically connected to one of the plurality of electrical connectors; iv. repeating steps i. through iii. until it has been determined whether the at least one characteristic of each of the plurality of electrical contacts is within a range that corresponds to the electrical contact being properly electrically connected to one of the plurality of electrical connectors, wherein the lead is determined to be MRI safe if it is determined that each of the plurality of electrical contacts is properly electrically connected to one of the plurality of electrical connectors.

An implantable electrical lead comprising: a) a lead body having a proximal end, a proximal portion and a distal portion; b) a plurality of electrodes located at the distal portion of the lead body; c) a plurality of electrical contacts located at the proximal portion of the lead body, wherein each of the plurality of electrical contacts has a contact length along the lead body; d) a plurality of insulating regions located at the proximal portion of the lead body, wherein each of the plurality of insulating regions has an insulating length along the lead body; and e) a plurality of conductive means that electrically couple the plurality of electrodes to the plurality of electrical contacts, wherein either one of the plurality of insulating lengths is different from the other insulating lengths, one of the plurality of contact lengths is different from the other contacts lengths, or some combination thereof.

BRIEF DESCRIPTION OF THE DRAWINGS

This disclosure may be more completely understood in consideration of the following detailed description of various embodiments of the disclosure in connection with the accompanying drawings, in which.

The figures provided herein are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawings that form a part hereof, and in which are shown by way of illustration several specific embodiments. It is to be understood that other embodiments are contemplated and are part of this disclosure. The following detailed description, therefore, is not to be taken in a limiting sense.

All scientific and technical terms used herein have meanings commonly used in the art unless otherwise specified. The definitions provided herein are to facilitate understanding of certain terms used herein and are not meant to limit the scope of the disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "implantable medical device" includes, for example, an implantable signal generator (ISG), a cardiac pacemaker, an implantable defibrillator, a congestive heart failure device, a hearing implant, a cochlear implant, a neurostimulator, a drug pump, a ventricular assist device, an insulin pump, an implantable sensing system, an artificial heart, a bone growth stimulator, or a prosthetic device, and the like.

Examples of "operably coupled" include, but are not limited to, electrically coupled, electrically connected, mechanically coupled, mechanically coupled, electrically and mechanically coupled, electrically and mechanically connected, and capable of being operably coupled.

Figure 1:
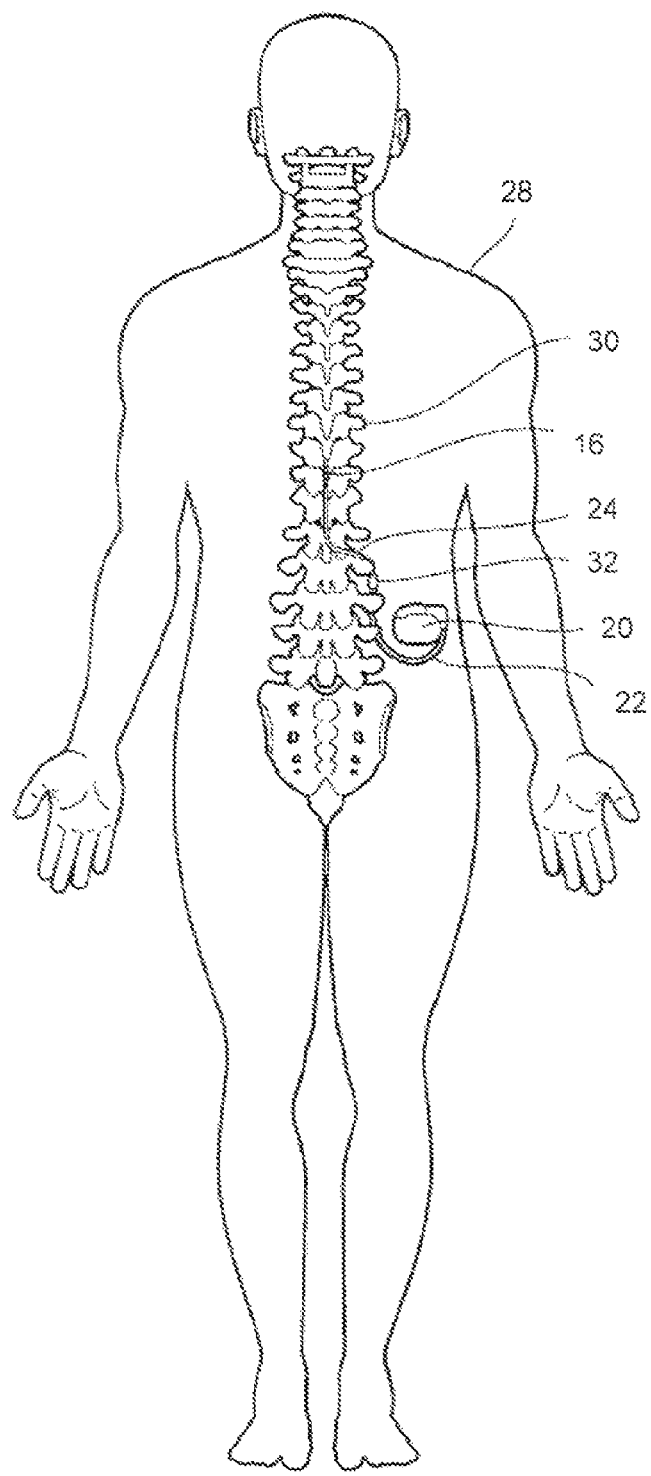
FIG. 1 is a schematic diagram of an active medical device implanted within a human body.

FIG. 1 is a schematic diagram of an implantable medical device 20 implanted within a human body or patient 28. The implantable medical device 20 is illustrated as an implantable signal generator (ISG) however; the implantable medical device 20 may be any implantable medical device as described above and can be placed in any location within a patient or on the surface of a patient's skin.

Figure 2:
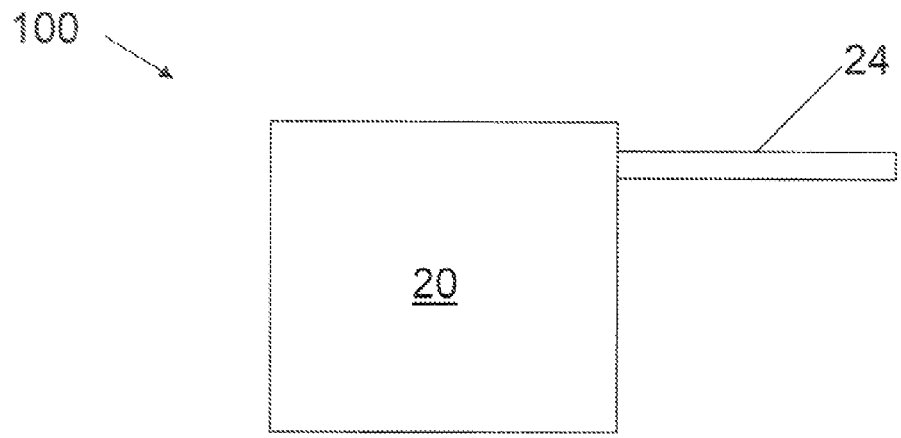
FIG. 2 is a diagrammatic representation of a side view of an implantable electrical signal therapy system.
Figure 3:
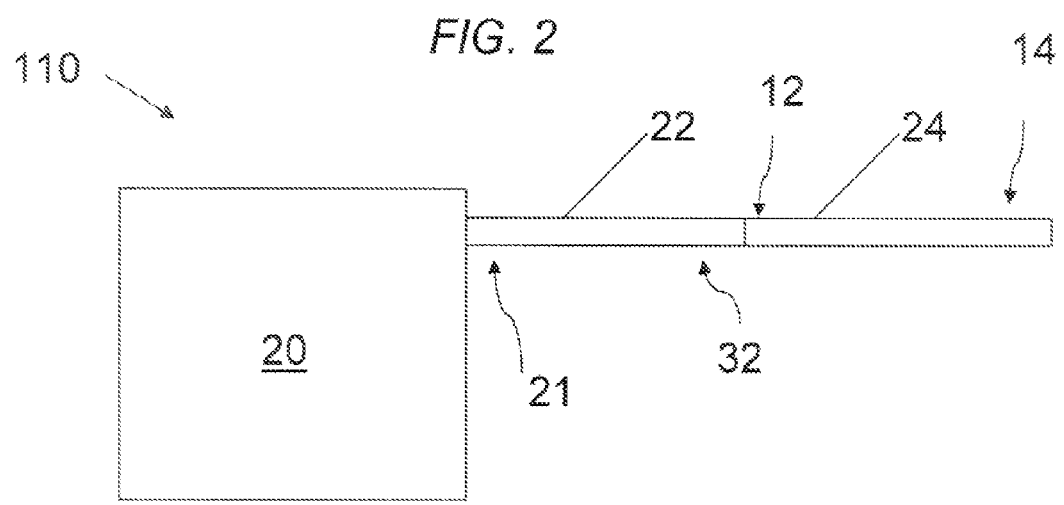
FIG. 3 is a diagrammatic representation of a side view of an implantable electrical signal therapy system.

FIG. 2 displays a representation of an implantable medical therapy system or implantable medical system 100. The system 100 comprises an ISG 20 and a lead 24 that is operably coupled to the ISG 20. The ISG 20 can be any electrical signal generator or similar implantable medical device useful for delivering therapy to a patient or for patient diagnostics. For example, ISG 20 may be a sensing device hearing implant; a signal generator such as a cardiac pacing device or defibrillator, a neurostimulator (such as a deep brain stimulator, a spinal cord stimulator, a subcutaneous stimulator, etc.), a gastric stimulator; or similar devices. FIG. 3 depicts a system 110 that comprises a lead extension 22 or other adaptor to couple lead 24 to ISG 20. While not shown, it will be understood by one of skill in the art, that more than one lead 24 may be operably coupled to one ISG 20 or one extension 22, or that more than one extension 22 may be operably coupled to one ISG 20. Generally, the lead extension 22 has a proximal end 21 coupled to the ISG 20, and distal end 32 coupled to the lead 24.

Figure 4:
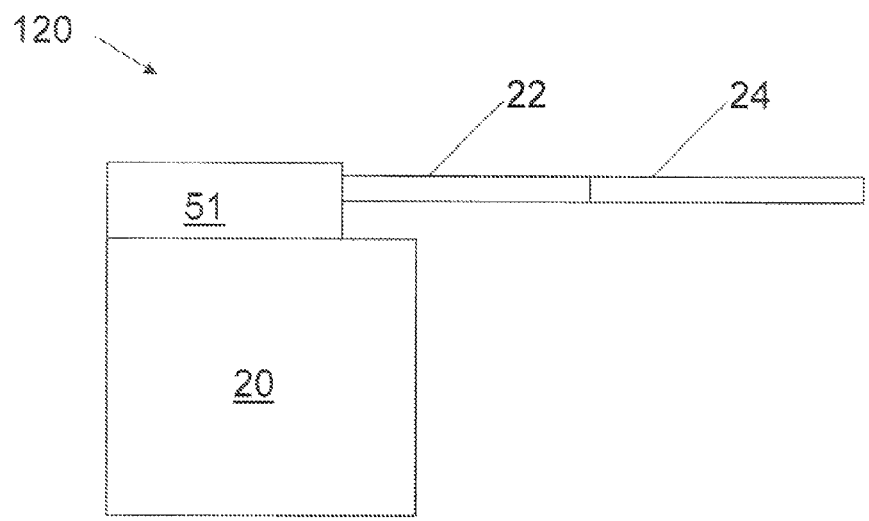
FIG. 4 is a diagrammatic representation of a portion of a connector block of a representative implantable electrical signal therapy system.

FIG. 4 displays another exemplary therapy system 120 that includes an ISG 20 having a connector block 51 connecting it to lead 24, or as displayed here extension 22 (or other adaptor) couples the lead 24 to the ISG 20. While not shown, it will be understood by one of skill in the art, that lead 24 may be coupled to ISG 20 without extension 22 or an adaptor.

Referring again to FIG. 1, an ISG 20 can be utilized with a lead extension 22 having a proximal end 21 coupled to the ISG 20, and a lead 24 having a proximal end coupled to a distal end 32 of the lead extension 22; and a distal end of the lead 24 that includes at least one electrode 16. In other embodiments, the proximal end of the lead 24 is coupled directly to the ISG 20, without using a lead extension 22. When a lead is referred to herein as connecting to an ISG, it will be understood by one of skill in the art that the lead can be connected to the ISG or the lead extension can be connected to the ISG. It will also be understood that portions of this disclosure that refer to components of the lead connecting to the ISG 20 can be referring to components of the lead or components of the lead extension connecting to the ISG 20. An "ISG connected component" can be used to generically refer to either a lead or a lead extension that can be operably coupled to the ISG 20.

The ISG 20 can be implanted in any useful region of the body such as in the abdomen of a patient 28. Similarly, the lead 24 can be implanted at any other useful region in the body, such as somewhere along the spinal cord 30. It will also be understood that a lead 24 as referred to herein can be modified to be used with other types of implantable medical devices and still be within the present disclosure.

Figure 5:
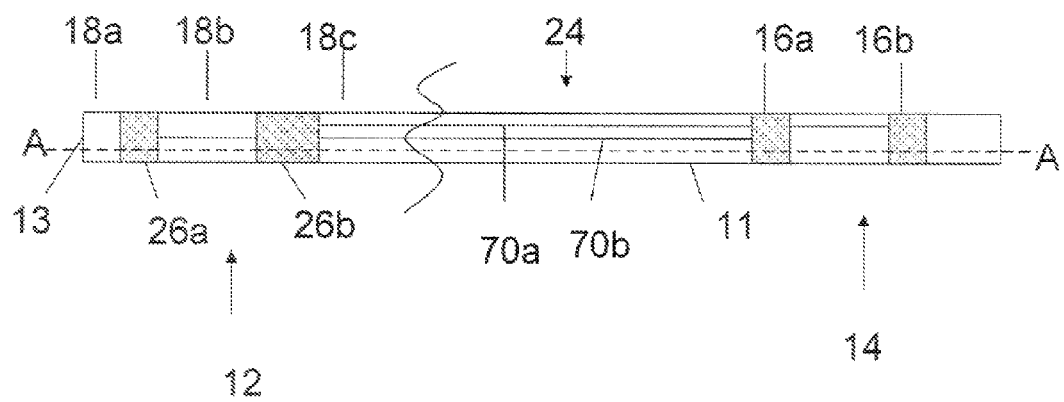
FIG. 5 is a diagrammatic representation of a portion of a lead.

FIG. 5 depicts a lead 24 that includes a lead body 11 having a proximal portion 12 with a proximal end 13, and a distal portion 14. The lead body 11 has a major axis (along the line A-A in FIG. 5) that runs generally from the distal portion 14 to the proximal portion 12.

The lead 24 includes at least one electrode 16. In one embodiment, the lead 24 includes a plurality of electrodes 16, illustrated as first electrode 16a, and second electrode 16b in FIG. 5. All multiple components referred to herein are considered to be "first", "second", and so on starting with the component that is closest to the proximal end 13 of the lead body. One of skill in the art will understand that the components could be designated from the other direction, or any other way, as well. The plurality of electrodes 16 are generally located at the distal portion 14 of the lead body 11. In one embodiment, a lead 24 having at least four electrodes is utilized. In another embodiment, a lead having at least eight electrodes is utilized. One of skill in the art will understand, having read this specification, that any types of electrodes normally utilized can be utilized herein. Examples of such electrodes include, but are not limited to, ring electrodes, coil electrodes, and segmented electrodes.

The lead 24 also includes at least one electrical contact 26. In an embodiment, the lead includes a plurality of electrical contacts 26. The at least one electrical contact 26 is generally located at the proximal portion 12 of the lead body 11. The example depicted in FIG. 5 depicts two electrical contacts, 26a and 26b, but one of skill in the art will understand that any number of electrical contacts can be utilized. One of skill in the art will also understand that the number of electrical contacts is at least partially dictated by the number of electrodes 16 on the distal end of the lead 24. In one embodiment, the lead 24 includes at least four electrical contacts. In another embodiment, a lead having at least eight electrical contacts utilized. In one embodiment, a lead has an equal amount of electrodes and electrical contacts. The electrical contacts 26 generally function to electrically connect the lead 24, and more specifically, the at least one electrode 16 of the lead 24 with the at least one electrical connector 56 of the connector block 51 (discussed below) when the lead is operably connected with the electrical connectors 56 of the connector block 51. Materials and methods of manufacturing electrical contacts including those generally utilized by one of ordinary skill in the art can be utilized in manufacturing leads in accordance with this disclosure.

The lead 24 also includes at least one insulating region 18. In an embodiment, the lead includes a plurality of insulating regions 18. The at least one insulating region 18 is generally located at the proximal portion 12 of the lead body 11. The example depicted in FIG. 5 includes three insulating regions, 18a, 18b and 18c, but one of skill in the art will understand that any number of insulating regions can be utilized. One of skill in the art will also understand that the number of insulating regions is at least partially dictated by the number of electrical contacts 26 of the lead 24. In one embodiment, there is one more insulating region than the number of electrical contacts. The insulating regions 18 generally function to electrically insulate the electrical contacts 26. Specifically, with regard to FIG. 5, insulating region 18b functions to electrically insulate the first electrical contact 26a, from the second electrical contact 26b. The insulating regions can also function to electrically isolate electrical contacts from other structures that they come in contact with. For example, the first insulating region 18a can function to electrically insulate the first electrical contact 26a from structures that the proximal end 13 comes in contact with. Materials and Methods of manufacturing insulating regions including those generally utilized by one of ordinary skill in the art can be utilized in manufacturing leads in accordance with this disclosure.

The lead 24 also includes at least one conductive element 70. In an embodiment, the lead includes a plurality of conductive elements. The conductive elements generally function to electrically connect the at least one electrode 16 to the at least one electrical contact 26. The conductive elements are generally located within the lead body 11 and generally traverse the lead body from the distal end to the proximal end (which is analogous to traversing the lead body from the proximal end to the distal end). The exemplary lead 24 depicted in FIG. 5 shows two conductive elements 70a, and 70b, however, one of skill in the art will understand that any number of conductive elements can be utilized. One of skill in the art will also understand that the number of conductive elements is at least partially dictated by the number of electrodes and electrical contacts. In one embodiment, there are an equal amount of electrodes, electrical contacts and conductive elements. Materials and methods of manufacturing conductive elements including those generally utilized by one of ordinary skill in the art can be utilized in manufacturing leads in accordance with this disclosure.

In one embodiment, the lead 24 includes a wire having insulation thereon and includes one or more conductive elements 70 each coupled at the proximal end of the lead body 11 to an electrical contact 26 and to electrodes 16 at the distal end of the lead body 11. Leads in accordance with this description can be designed to be inserted into a patient percutaneously, surgically implanted, or other implantation methods. In some embodiments, the lead 24 may contain a paddle at its distal end for housing electrodes 16. In many embodiments, the lead 24 may include one or more ring electrodes at the distal end of the lead 24.

Figure 6:
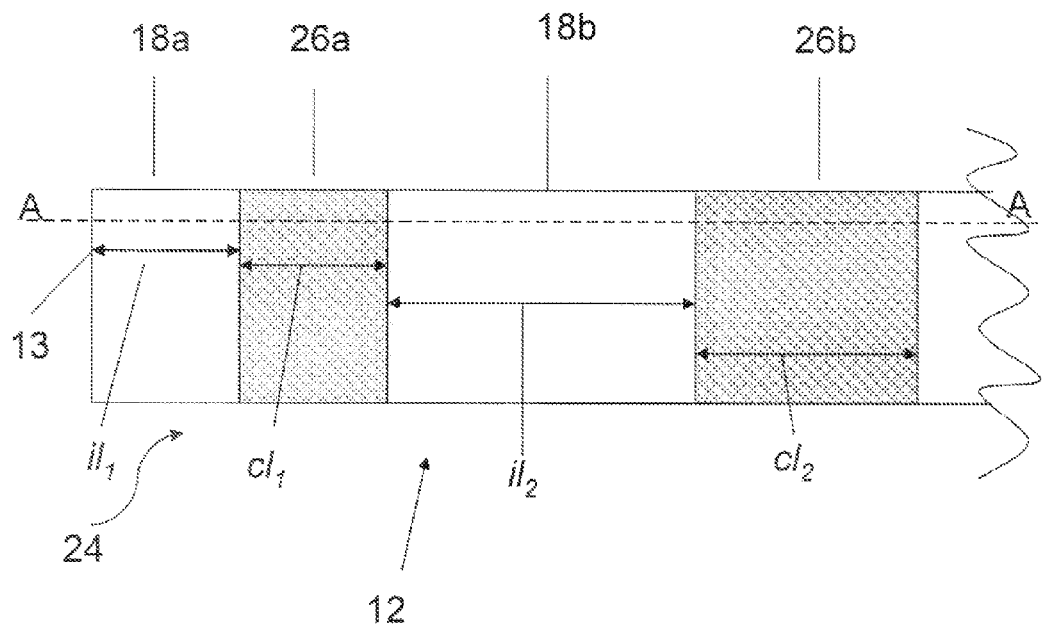
FIG. 6 is a diagrammatic representation of a portion of a lead.

Each electrical contact 26 has a contact length cl along the major axis A-A of the lead body 11. FIG. 6 illustrates the contact length $cl_1$ of the first electrical contact 26a and the contact length $cl_2$ of the second electrical contact 26b. Generally, the contact length cl of an electrical contact ranges from about 0.005 inches (0.012 cm) to about 0.5 inches (1.3 cm). In one embodiment, the contact length cl of an electrical contact ranges from about 0.01 inches (0.025 cm) to about 0.3 inches (0.76 cm). In another embodiment, the contact length cl of an electrical contact ranges from about 0.03 inches (0.76 cm) to about 0.15 inches (0.38 cm).

Each insulating region 18 has an insulating length il along the major axis A-A of the lead body 11. FIG. 6 illustrates the insulating length $il_1$ of the first insulating region 18a and the insulating length $il_2$ of the second insulating region 18b. Generally, the insulating length il of an insulating region ranges from 0.005 inches (0.012 cm) to about 0.5 inches (1.3 cm). In one embodiment, the insulating length il of an insulating region ranges from about 0.01 inches (0.025 cm) to about 0.3 inches (0.76 cm). In another embodiment, the insulating length il of an insulating region ranges from about 0.03 inches (0.76 cm) to about 0.15 inches (0.38 cm).

Generally, the electrical contacts 26 and the insulating regions 18 are configured so that the insulating regions electrically isolate the electrical contacts. Generally, such a purpose implies that the electrical contacts and the insulating regions alternate along the major axis of the lead body. FIGS. 5, 6, 8, and 9 show exemplary configurations in which the electrical contacts and the insulating regions alternate along the major axis of the lead body.

Exemplary leads generally have one of the plurality of insulating lengths different from the other insulating lengths; or have one of the plurality of contact lengths different from the other contact lengths. One of skill in the art will understand, having read this specification, that any number of insulating lengths different from the others, any number of contact lengths different from the others, or any combination thereof are entirely appropriate. In an embodiment, at least one of the insulating lengths is different from the other insulating lengths. In an embodiment having x number of insulating lengths, at least one, two, three, four, five . . . x−2 insulating lengths are different than the other insulating lengths. In an embodiment, at least one of the contact lengths is different from the other contact lengths. In an embodiment, at least two of the contact lengths are different from the other contact lengths. In an embodiment having y number of contact lengths, at least three, four, five . . . y−2 contact lengths are different that the other contact lengths. In an embodiment, at least one insulating length can be different from the other insulating lengths, and at least one contact length can be different from the other contact lengths. In an embodiment, the number of insulating lengths that are different than the other insulating lengths can be the same or different than the number of contact lengths that are different than the other contact lengths.

Disclosed herein is an implantable electrical lead comprising: a) a lead body having a proximal end, a proximal portion and a distal portion; b) a plurality of electrodes located at the distal portion of the lead body; c) a plurality of electrical contacts located at the proximal portion of the lead body, wherein each of the plurality of electrical contacts has a contact length along the lead body; d) a plurality of insulating regions located at the proximal portion of the lead body, wherein each of the plurality of insulating regions has an insulating length along the lead body; and e) a plurality of conductive means that electrically couple the plurality of electrodes to the plurality of electrical contacts, wherein either one of the plurality of insulating lengths is different from the other insulating lengths, one of the plurality of contact lengths is different from the other contacts lengths, or some combination thereof.

Leads as discussed herein can be utilized as part of an implantable therapy delivery system, examples of which were illustrated in FIGS. 2, 3, and 4. Such implantable therapy delivery systems include at least one lead as discussed above, an optional lead extension, an optional adaptor, and an implantable medical device, such as an implantable signal generator (ISG). Although portions of this specification refer to an ISG, one of skill in the art will also understand that other implantable medical devices can also be utilized herein.

Figure 7:
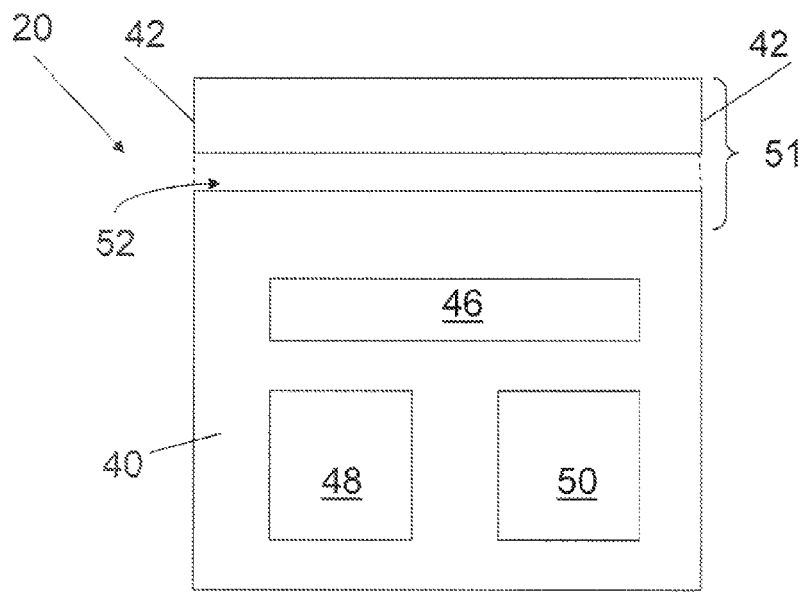
FIG. 7 is a diagrammatic representation of an implantable signal generator (ISG).

One embodiment of an ISG 20 is depicted in FIG. 7. The ISG 20 depicted in FIG. 7 includes a housing 40. The housing 40 generally functions to contain at least some of the components of the ISG 20. In one embodiment, the housing 40 can generally be of a rectangular type shape. The ISG 20 is operably coupled to the electronic circuitry 46 that generally functions to control the ISG 20. In one embodiment, the electronic circuitry 46 is housed within the housing 40 of the ISG 20 (depicted in FIG. 7). In another embodiment, the electronic circuitry 46 is not contained within the housing 40, but is still operably coupled to the ISG 20. The ISG 20 is also operably coupled to a power source 48. The power source 48 can be contained within the housing 40 (depicted in FIG. 7) or can be outside the housing 40, but still be operably coupled to the ISG 20. The power source 48 can be a battery or an inductive coil, or other such components known to those of skill in the art. In one embodiment, the ISG 20 is also operably coupled to memory 50. In one embodiment, the memory 50 is contained within the housing 40 (depicted in FIG. 7), and in another embodiment, the memory 50 is outside the housing 40 but is still operably coupled to the ISG 20.

The ISG 20 also includes an operably coupled connector block 51. The connector block 51 can be separate from the ISG 20 but be permanently or releasably operably coupled to the housing 40, or the connector block 51 can be integral with the housing 40 and can be a designated portion of the housing 40 (depicted in FIG. 7). The connector block 51 includes a lumen 52 that extends through the connector block 51 from one surface of the connector block 51 to another surface of the connector block 51. A single ISG 20 can include more than one connector block 51, a connector block can have more than one lumen 52, or both. In one embodiment, the lumen 52 extends through the connector block 51 from the first surface 42 to the second surface 44. The lumen 52 is generally configured to receive at least a portion of a lead within at least a portion of the lumen 52. The lumen 52 can also be configured to receive more than one lead.

The housing 40 and the connector block 51 can be made of any material commonly known to those of skill in the art, including but not limited to titanium, and other such metals. In one embodiment, the material that makes up the housing and the connector block are a biocompatible material. Exemplary materials include those that are utilized in implantable signal generators available from Medtronic, Inc (Minneapolis, Minn.). It will also be understood by one of skill in the art that possible configurations and dimensions of the housing 40 of the ISG 20 are generally known and can, but need not be utilized. Exemplary configurations and materials include those that are utilized in implantable signal generators available from Medtronic, Inc (Minneapolis, Minn.). One embodiment of an ISG 20 that can be utilized has a housing 40 and a connector block 51 that are integrally formed. In such an embodiment, the connector block is a separate portion of the housing that contains the lumen. The connector block 51 and the housing 40 can be made of the same type of material, can be made from the same piece of material, or can be made of separate materials and can be operably coupled together. In some embodiments, the connector block is a separate piece that is joined to the housing. In some embodiments, the connector block is a portion of the housing and is only distinguished by being the portion of the housing 40 that contains the lumen 52.

The electronic circuitry 46 that is operably coupled to the ISG 20 can generally be similar to those known to one of skill in the art. Examples of such can be found in implantable signal generators available from Medtronic, Inc. (Minneapolis, Minn.). The power source 48 of the ISG 20 can also generally be similar to that known to those of skill in the art. Examples of such can be found in implantable signal generators available from Medtronic, Inc. (Minneapolis, Minn.). The memory 50 can generally include any magnetic, electronic, or optical media, such as random access memory (RAM), read-only memory (ROM), electronically-erasable programmable ROM (EEPROM), flash memory, or the like, or a combination thereof. Examples of such can be found in implantable signal generators available from Medtronic, Inc.

Figure 8:
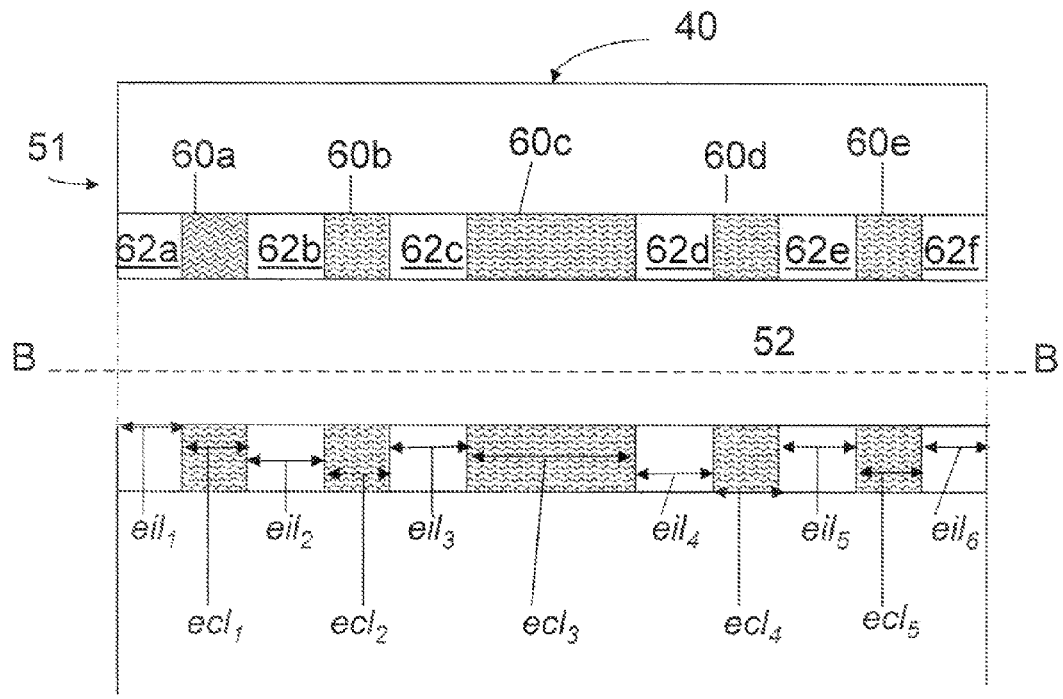
FIG. 8 is a diagrammatic representation of a cross section of a portion of an ISG.

As seen in FIG. 8, the lumen 52 of the connector block 51 has a major axis, shown as line B-B. The major axis generally runs along the lumen 52 from the first surface 42 to the second surface 44 (depicted in FIG. 7). The connector block 51 also includes at least one electrical connector 60. The connector block 51, the lumen 52, and the at least one electrical connector 60 are generally configured so that the electrical connector 60 can be electrically connected to a lead that is placed within the lumen 52. This generally implies that at least a portion of the material that makes up electrical connector 60 is exposed on the interior surface of the lumen 52. The example depicted in FIG. 8 depicts five electrical connectors 60a, 60b, 60c, 60d, and 60e, but one of skill in the art will understand that any number of electrical connectors can be utilized. One of skill in the art will also understand that the number of electrical connectors is at least partially dictated by the number of electrical contacts on leads that are meant to be utilized with the ISG 20. In one embodiment, the connector block 51 includes at least four electrical connectors. In another embodiment, a connector block 51 having at least eight electrical connectors is utilized. In one embodiment, a connector block has an equal amount of electrical connectors as the lead that is to be used with the connector block has electrical contacts.

The electrical connectors 60 are generally configured to be operably coupled to the electronic circuitry 46. The electrical connectors 60 generally function to electrically connect the lead 24, and more specifically, the at least one electrode contact 26 of the lead 24 with the electronic circuitry 46. Furthermore, the electrical connectors 60 function to electrically connect the electrodes 16 of a lead 24 that is operably inserted into the connector block 51 to the electronic circuitry 46 of the ISG 20. Materials and methods of manufacturing electrical connectors including those generally utilized by those of ordinary skill in the art can be utilized in manufacturing connector blocks in accordance with this disclosure.

The electrical connectors 60 can include material configured to provide electrical contact. In one embodiment, the electrical connector 60 can also mechanically stabilize the lead and/or the electrical contact that the electrical connector 60 is in contact with. Materials and configurations that can be utilized as electrical connectors 60 are known to those of skill in the art. Examples of such configurations include, but are not limited to set screws made of an electrically conductive material, coil springs that can make electrical contact, friction fit contacts (also referred to as wiping contacts or beam contacts), or similar devices. A specific example of a coil spring that can make an electrical contact is a Bal Seal contact ring available from Bal Seal Engineering Co. Inc (Foothill Ranch, Calif.). Other examples of such devices can be found in implantable signal generators available from Medtronic, Inc. (Minneapolis, Minn.) for example. In one embodiment, a combination of more than one type of electrical connector 60 can be housed in the lumen 52. In one embodiment, both set screws and coil springs that make electrical contact can be utilized in a lumen 52.

The connector block 51 also includes at least one electrical insulators 62. The connector block 51, the lumen 52, the at least one electrical connector 60, and the at least one electrical insulator 62 are generally configured so that the electrical connector 60 can be electrically connected to a lead that is placed within the lumen 52, and the electrical connection is insulated from surrounding portions of the device. This generally implies that at least a portion of the material that makes up the at least one electrical insulator 62 is exposed on the interior surface of the lumen 52. The example depicted in FIG. 8 depicts five electrical insulators 62a, 62b, 62c, 62d, 62e, and 62f, but one of skill in the art will understand that any number of electrical insulators can be utilized. One of skill in the art will also understand that the number of electrical insulators is at least partially dictated by the number of electrical connectors 60 in the lumen 52 In one embodiment, there is one more electrical insulator than the number of electrical connectors. The electrical insulators 62 generally function to electrically insulate the electrical connectors 60. Specifically, with regard to FIG. 8, electrical insulator 60b functions to electrically insulate the first electrical connector 60a, from the second electrical connector 62b. The electrical insulators can also function to electrically isolate electrical connectors from other structures that they come in contact with. For example, the first electrical insulator 62a can function to electrically insulate the first electrical connector 60a from structures that may be present at the end of the lumen 52. Materials and methods of manufacturing electrical insulators including those generally utilized by one of ordinary skill in the art can be utilized in manufacturing connector blocks in accordance with this disclosure.

Each electrical connector 60 has an electrical connector length ecl along the major axis B-B of the lumen 52. FIG. 8 illustrates the electrical connector length $ecl_1$ of the first electrical connector 60a and the electrical connector length $ecl_2$ of the second electrical connector 60b. Generally, the electrical connector length ecl of an electrical connector ranges from about 0.005 inches (0.012 cm) to about 0.5 inches (1.3 cm). In one embodiment, the electrical connector length ecl of an electrical connector ranges from 0.01 inches (0.025 cm) to about 0.3 inches (0.76 cm). In another embodiment, the electrical contact length ecl of an electrical connector ranges from about 0.03 inches (0.76 cm) to about 0.15 inches (0.38 cm).

Each electrical insulator 62 has an electrical insulator length eil along the major axis B-B of the lumen 52. FIG. 8 illustrates the electrical insulator length $eil_1$ of the first electrical insulator 62a and the electrical insulator length $eil_2$ of the second electrical insulator 62b. Generally, the electrical insulator length eil of an electrical insulator ranges from about 0.005 inches (0.012 cm) to about 0.5 inches (1.3 cm). In one embodiment, the electrical insulator length eil of an electrical insulator ranges from 0.01 inches (0.025 cm) to about 0.3 inches (0.76 cm). In another embodiment, the electrical insulator length eil of an electrical insulator ranges from about 0.03 inches (0.76 cm) to about 0.15 inches (0.38 cm).

Figure 9:
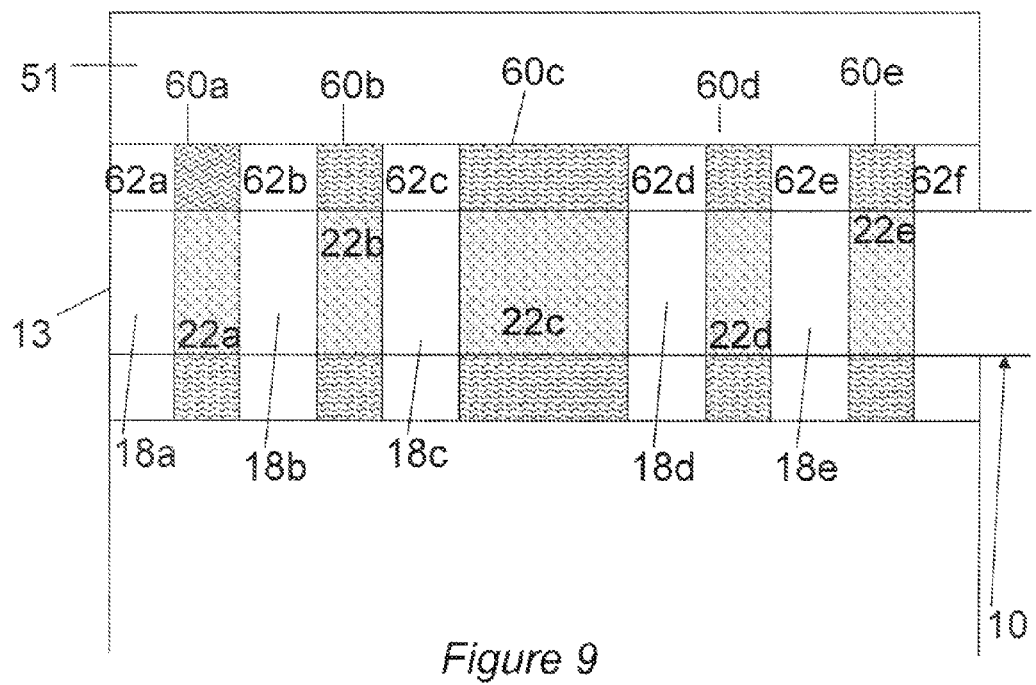
FIG. 9 is a diagrammatic representation of a cross section of a lead operably coupled with an ISG.

Generally, the electrical connectors 60 and the electrical insulators 62 are configured so that the electrical insulators electrically isolate the electrical connectors. Generally, such a purpose implies that the electrical connectors and the electrical insulators alternate along the major axis of the lumen of the connector block. FIGS. 8 and 9 show exemplary configurations in which the electrical connectors and the electrical insulators alternate along the major axis of the lumen of the connector block.

Exemplary connector blocks generally have one of the plurality of electrical insulator lengths different from the other electrical insulator lengths; or have one of the plurality of electrical connector lengths different from the other electrical connector lengths. One of skill in the art will understand, having read this specification, that any number of electrical insulator lengths different from the others, any number of electrical connector lengths different from the other, or any combination thereof are entirely appropriate. In an embodiment, at least one of the electrical insulator lengths is different from the other electrical insulator lengths. In an embodiment having x number of electrical insulator lengths, at least one, two, three, four, five . . . x−2 electrical insulator lengths are different than the other electrical insulator lengths. In an embodiment, at least one of the electrical connector lengths is different from the other electrical connector lengths. In an embodiment having y number of electrical connector lengths, at least one, two, three, four, five . . . y−2 electrical connector lengths are different that the other electrical connector lengths. In an embodiment, at least one electrical insulator lengths can be different from the other electrical insulator lengths, and at least one electrical connector lengths can be different from the other electrical connector lengths. In an embodiment, the number of electrical insulator lengths that are different than the other electrical insulator lengths can be the same or different than the number of electrical connector lengths that are different than the other electrical connector lengths.

FIG. 9 depicts a lead as described herein operably inserted into a lumen of a connector block as described herein. As seen in FIG. 9, the plurality of electrical contacts 22 and the plurality of insulating regions 18 on the lead; and the plurality of electrical connectors 60 and the plurality of electrical insulators 62 in the connector block are configured so that each of the electrical contacts form operable connections to the electronic circuitry through each of the plurality of electrical connectors, and the insulating regions and the electrical insulators electrically isolate adjacent operable connections. In one embodiment, the lead and the connector block, or more specifically the insulating regions and the electrical contacts on the lead; and the electrical insulators and the electrical connectors on the connector block form mirror images of each other. In this way, a lead and connector block that are configured to be utilized with each other have electrical contacts and electrical connectors; and insulating regions and electrical insulators that align along the major axes of the lead and the lumen respectively. An example of such alignment can be seen in FIG. 9. One of skill in the art, having read this specification, will understand that any combination of different contact lengths and electrical connector lengths; and insulating lengths and electrical insulator lengths can be utilized as long as the electrical contacts align with the electrical connectors and the insulating regions align with the electrical insulator regions when the lead is operably inserted into the lumen of the connector block.

In an embodiment, the plurality of insulating lengths are substantially the same as the plurality of electrical insulator lengths and the plurality of contact lengths are substantially the same as the plurality of connector lengths. In an embodiment, one of the plurality of insulating lengths is different from the other insulating lengths and one of the plurality of electrical insulator lengths is different from the other electrical insulator lengths. In an embodiment, one of the plurality of contact lengths is different from the other contact lengths and one of the plurality of electrical connector lengths is different from the other electrical connector lengths. In an embodiment, more than one of the plurality of insulating lengths is different from the other insulating lengths and more than one of the plurality of electrical insulator lengths is different from the other electrical insulator lengths. In an embodiment, more than one of the plurality of contact lengths is different from the other contact lengths and more than one of the plurality of electrical connector lengths is different from the other electrical connector lengths. In an embodiment, the insulating region that is closest to the proximal end of the lead has a different insulating length than at least one of the other insulating lengths.

Such a system can also optionally include a physician programmer and a patient programmer (not shown). In one embodiment, the ISG 20 can include an implantable signal generator of the type available from Medtronic, Inc., which is generally capable of generating multiple pulses occurring either simultaneously or one pulse shifting in time with respect to the other, and having independently varying amplitudes and pulse widths. The ISG 20 is operably coupled to a power source and the electrical circuitry for sending precise, electrical pulses to the patient to provide a desired treatment or therapy. While the ISG 20, in many embodiments, provides electrical stimulation by way of pulses, other forms of stimulation may be used such as continuous electrical stimulation.

One embodiment includes an ISG that contains or is operably coupled to a computer readable medium containing instructions for carrying out a process to determine whether each of the at least one electrical contacts is properly electrically connected to the plurality of electrical connectors. In an embodiment, the determination of whether each of the at least one electrical contacts is properly electrically connected to the plurality of electrical connectors can also determine whether the lead is an MRI safe lead.

Figure 10:
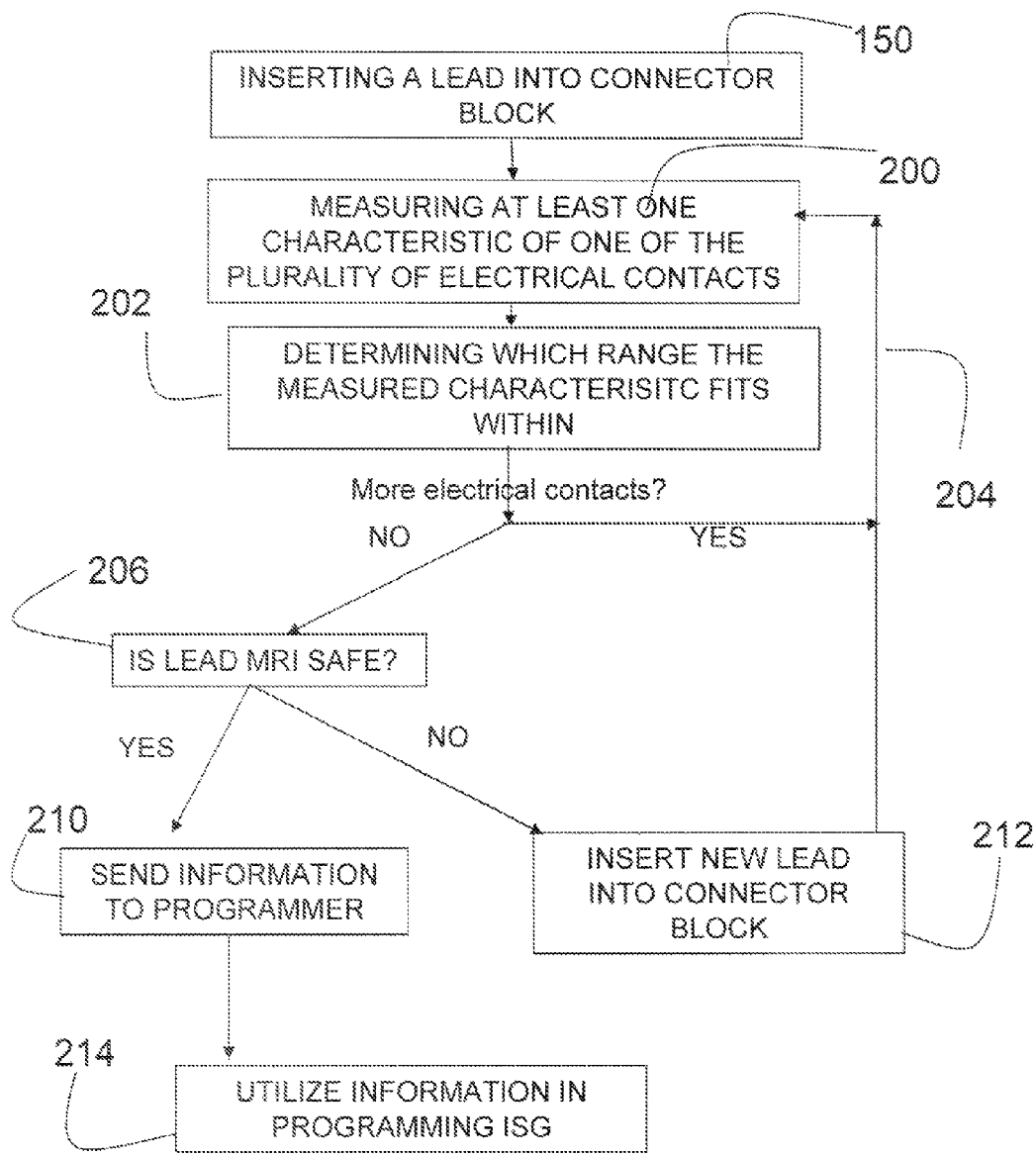
FIG. 10 illustrates methods as disclosed herein.

The process can also be carried out in other fashions, i.e., the instructions do not need to be housed in memory on the ISG 20. The steps of the process are illustrated in FIG. 10. As seen therein, the process includes a step 200 of measuring at least one characteristic of at least one of the plurality of electrical contacts. Exemplary characteristics that can be measured include, but are not limited to, impedance, and potential across the electrical contacts. In one embodiment impedance is measured. One of skill in the art, having read this specification will understand how to measure at least one characteristic.

The process also includes a step 202 of determining which range the measured characteristic is within. For example, in an embodiment where impedance is the characteristic that is measured, checking the impedance of one of the electrical contacts will either return an impedance value that is characteristic of an electrical connector being properly connected thereto, or a value that is characteristic of an electrical connector not being properly connected thereto. As used herein, an electrical connector begin properly connected to an electrical contact refers to a situation wherein the lead is operably inserted into the lumen of the connector block, and substantially the entire surface area of the electrical contact of the lead is in contact with substantially the entire surface of one electrical connector of the connector block, and there is no substantial portion of an insulating region in contact with the electrical contact. An electrical contact being "properly connected" is not frustrated by normal tolerances of lead and connector block manufacturing processes.

In one embodiment of the process, if there are more electrical contacts that have not been measured, the process can also optionally include the step 204 that measures another characteristic of at least one of the plurality of electrical contacts until all of the electrical contacts have been checked. One embodiment of the process stops measuring the at least one characteristic of the electrical contacts when or if it is determined that one of the electrical contacts is not properly connected to an electrical connector. In one embodiment, at least one characteristic of all of the electrical contacts are measured. In one embodiment, at least one characteristic of all of the electrical contacts have been measured, it can then be determined whether the lead is MRI safe or not. Such a determination is based on all of the electrical contacts being properly connected to the electrical connectors. If the lead is found to be MRI safe, this information can optionally be transmitted to a programmer, exemplified by optional step 210 in FIG. 10. The information can also optionally be utilized during the programming of the device, exemplified by optional step 214 in FIG. 10.

A process of determining whether a lead that has been operably coupled to an implantable signal generator is an MRI safe lead comprises inserting a lead into the connector block of the implantable signal generator; measuring at least one characteristic of one of the plurality of electrical contacts; determining whether the at least one measured characteristic of the one of the plurality of electrical contacts is within a range that corresponds to the electrical contact being properly electrically connected to the one of the plurality of electrical connectors; and repeating those steps until it has been determined whether the at least one characteristic of each of the plurality of electrical contacts is within a range that corresponds to the electrical contact being properly electrically connected to the one of the plurality of electrical connectors, wherein the lead is determined to be MRI safe if it is determined that each of the plurality of electrical contacts is properly electrically connected to one of the plurality of electrical connectors.

A method of determining if a lead that has been operably coupled to an ISG is an MRI safe lead includes the preliminary step of inserting a lead, this is exemplified by step 150 in FIG. 10. Alternatively, if the first lead that was inserted into the connector block was not found to be MRI safe, that lead can be removed, and another lead can be inserted into the connector block. This step is exemplified by step 212 in FIG. 10. The process can then be begun again by commencing step 200, as exemplified in FIG. 10.

Leads, connector blocks, and methods as described herein can offer an advantage in that they provide a lockout that can enhance the likelihood that only MRI safe components are utilized with other MRI safe components. For example, a connector block (or a lead) may only be able to be operably coupled to a lead (or a connector block) that has complementary component lengths. Such a configuration could ensure that leads other than the desired leads, i.e. MRI safe leads, would not be able to be implanted and utilized in an incorrect system. The component lengths of the lead body and the connector block could also offer a visual indicator that a component is of a particular variety, for example, an MRI safe lead and connector block. The methods described herein offer a process to check whether the leads and connector blocks are aligned, which can be used to determine if a MRI safe lead is being implanted and operably coupled to a connector block in a MRI safe ISG, MRI safe lead extension or MRI safe lead adaptor.

Thus, embodiments of an implantable medical electrical lead and connector assembly are disclosed. One skilled in the art will appreciate that the present disclosure can be practiced with embodiments other than those disclosed. The disclosed embodiments are presented for purposes of illustration and not limitation.

What is claimed is:

1. An implantable system comprising:
   a lead, wherein the lead comprises:
   a) a lead body having a proximal end, a proximal portion, a distal portion, and a major axis;
   b) a plurality of electrodes located at the distal portion of the lead body;
   c) a plurality of electrical contacts located on an outer surface at the proximal portion of the lead body, wherein each of the plurality of electrical contacts has a contact length along the major axis of the lead body;
   d) a plurality of insulating regions located at the proximal portion of the lead body, wherein each of the plurality of insulating regions has an insulating length along the major axis of the lead body; and
   e) a plurality of conductive elements that operably couple the plurality of electrodes to the plurality of electrical contacts,
   wherein the plurality of the electrical contacts and the plurality of the insulating regions are configured so that the plurality of insulating regions electrically isolate the electrical contacts, and wherein either one of the plurality of insulating lengths is different from the other insulating lengths or one of the plurality of contact lengths is different from the other contact lengths; and an implantable signal generator, wherein the implantable signal generator comprises:
   a) electronic circuitry; and
   b) a connector block comprising:
      i. a lumen having a major axis, wherein the lumen is configured to receive at least a portion of the lead;
      ii. a plurality of electrical connectors each having an electrical connector length along the major axis of the lumen, wherein the plurality of electrical connectors are operably coupled to the electronic circuitry,
      iii. a plurality of electrical insulators each having an electrical insulator length along the major axis of the lumen,
      wherein either one of the plurality of electrical connector lengths is different from the other electrical connector lengths or one of the plurality of electrical insulator lengths is different from the other electrical insulator lengths,
   wherein the plurality of electrical contacts and the plurality of insulating regions on the lead, and the plurality of electrical connectors and the plurality of electrical insulators in the connector block are configured so that the lengths of the plurality of electrical connectors are the same lengths as the lengths of the corresponding electrical contacts and so that the plurality of electrical contacts form operable connections to the electronic circuitry through the plurality of electrical connectors, and the insulating regions and the electrical insulators electrically isolate adjacent operable connections.

2. The implantable medical system according to claim 1, wherein one of the plurality of insulating lengths is different from the other insulating lengths and one of the plurality of electrical insulator lengths is different from the other electrical insulator lengths.

3. The implantable medical system according to claim 1, wherein one of the plurality of contact lengths is different from the other contact lengths and one of the plurality of electrical connector lengths is different from the other.

4. The implantable medical system according to claim 1, wherein more than one of the plurality of insulating lengths is different from the other insulating lengths and more than one of the plurality of electrical insulator lengths is different from the other electrical insulator lengths.

5. The implantable medical system according to claim 1, wherein more than one of the plurality of contact lengths is different from the other contact lengths and more than one of the plurality of electrical connector lengths is different from the other electrical connector lengths.

6. The implantable medical system according to claim 1, wherein the insulating region that is closest to the proximal end of the lead has an insulating length that is different than at least one of the other insulating lengths.

7. The implantable medical system according to claim 1, wherein the electronic circuitry is configured to carry out a process to determine whether the plurality of electrical contacts is properly electrically connected to the plurality of electrical connectors.

8. The implantable medical system according to claim 1 further comprising a non-transitory computer readable medium containing instructions for carrying out a process to determine whether the plurality of electrical contacts is properly electrically connected to the plurality of electrical connectors.

9. The implantable medical system according to claim 8, wherein the process comprises:

measuring at least one characteristic of one of the plurality of electrical contacts; and determining whether the at least one measured characteristic of the one of the plurality of electrical contacts is within a range that corresponds to the electrical contact being properly electrically connected to one of the plurality of electrical connectors.

10. The implantable medical system according to claim 1, wherein the plurality of electrodes have a same diameter.

* * * * *